United States Patent
Menozzi et al.

(10) Patent No.: US 9,963,575 B2
(45) Date of Patent: May 8, 2018

(54) STERICALLY HINDERED AMINE LIGHT STABILIZERS WITH A MIXED FUNCTIONALIZATION

(71) Applicant: BASF SE, Ludwigshafen (DE)

(72) Inventors: Edoardo Menozzi, Basel (CH); Kai-Uwe Schoning, Oberwil (CH)

(73) Assignee: BASF SE, Ludwigshafen (DE)

( * ) Notice: Subject to any disclaimer, the term of this patent is extended or adjusted under 35 U.S.C. 154(b) by 0 days. days.

(21) Appl. No.: 15/389,823

(22) Filed: Dec. 23, 2016

(65) Prior Publication Data

US 2017/0107352 A1 Apr. 20, 2017

Related U.S. Application Data

(63) Continuation of application No. 13/879,114, filed as application No. PCT/EP2011/068059 on Oct. 17, 2011, now Pat. No. 9,550,941.

(Continued)

(30) Foreign Application Priority Data

Oct. 20, 2010 (EP) .................................... 10188235

(51) Int. Cl.
| | | |
|---|---|---|
| *C09K 15/30* | (2006.01) | |
| *C08K 5/3492* | (2006.01) | |
| *C07D 401/14* | (2006.01) | |
| *C08K 3/00* | (2018.01) | |

(52) U.S. Cl.
CPC ........ *C08K 5/34926* (2013.01); *C07D 401/14* (2013.01); *C09K 15/30* (2013.01); *C08K 3/0033* (2013.01)

(58) Field of Classification Search
CPC ..................................................... C09K 15/20
See application file for complete search history.

(56) References Cited

U.S. PATENT DOCUMENTS

| | | | |
|---|---|---|---|
| 5,198,130 A | 3/1993 | Schumacher | |
| 5,202,441 A | 4/1993 | Suhadolnik et al. | |
| 5,204,443 A | 4/1993 | Winter et al. | |
| 5,705,083 A | 1/1998 | Wyss et al. | |
| 5,980,783 A | 11/1999 | Gugumus | |
| 6,117,995 A | 9/2000 | Zedda et al. | |
| 9,550,941 B2 * | 1/2017 | Menozzi ............... | C07D 401/14 |
| 2005/0049337 A1 | 3/2005 | Stretanski et al. | |
| 2010/0324182 A1 | 12/2010 | Roth | |
| 2012/0083557 A1 | 4/2012 | Schoening | |
| 2012/0108709 A1 | 5/2012 | Schoening | |
| 2012/0108711 A1 | 5/2012 | Sale et al. | |
| 2012/0178829 A1 | 7/2012 | Hauck et al. | |
| 2012/0232197 A1 | 9/2012 | Menozzi et al. | |
| 2013/0041076 A1 | 2/2013 | Meier et al. | |
| 2013/0053484 A1 | 2/2013 | Meier et al. | |

FOREIGN PATENT DOCUMENTS

| | | |
|---|---|---|
| CN | 1235159 | 11/1999 |
| CN | 1608103 | 4/2005 |

(Continued)

OTHER PUBLICATIONS

Copending U.S. Appl. No. 13/879,107, filed Apr. 12, 2013.

*Primary Examiner* — Peter F Godenschwager
(74) *Attorney, Agent, or Firm* — Oblon, McClelland, Maier & Neustadt, L.L.P.

(57) ABSTRACT

Disclosed herein is a compound of the formula (I), wherein one or two radicals of the radicals $R_1$ are independently of one another $C_1$-$C_{20}$alkyloxy or $C_3$-$C_{12}$cycloalkyloxy and the remaining radicals $R_1$ are independently of one another hydrogen, C1-$C_{20}$alkyl or $C_3$-$C_{12}$cycloalkyl; the radicals $R_0$ and $R_2$ are independently of one another hydrogen, $C_1$-$C_{20}$alkyl, $C_3$-$C_{12}$cycloalkyl or a group of the formula (II-a) with $R_3$ being hydrogen, $C_1$-$C_{20}$alkyl, $C_3$-$C_{12}$cycloalkyl, $C_1$-$C_{20}$alkyloxy or $C_3$-$C_{12}$cycloalkyloxy; Y is $C_2$-$C_{12}$alkylene; m is 0 or 1; n is 1, 2 or 3; when n is 1, X is hydrogen, $C_1$-$C_{20}$alkyl, $C_3$-$C_{12}$cycloalkyl or a group of the formula (II-a); when n is 2, X is $C_2$-$C_{12}$alkylene; when n is 3, X is a group N(Z—)$_3$ with Z being $C_2$-$C_{12}$alkyl.

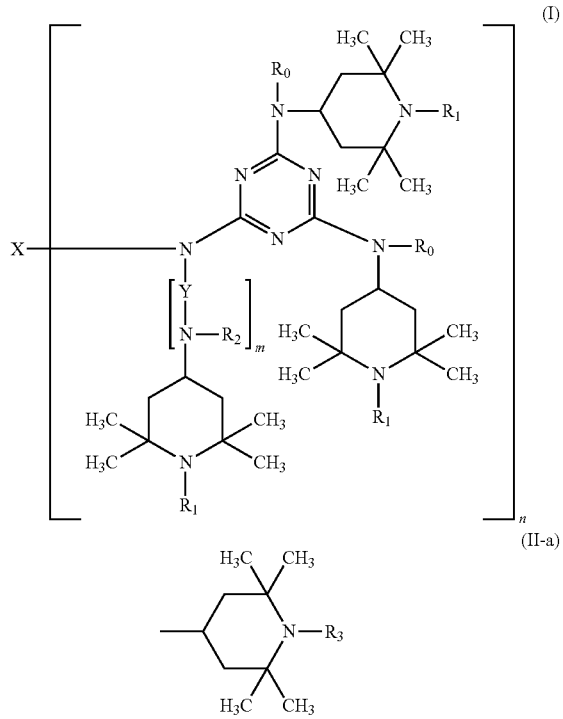

13 Claims, No Drawings

Related U.S. Application Data

(60) Provisional application No. 61/394,797, filed on Oct. 20, 2010.

(56) References Cited

FOREIGN PATENT DOCUMENTS

| | | |
|---|---|---|
| EP | 2319832 | 5/2011 |
| JP | 7-252500 | 10/1995 |
| JP | 8-283586 | 10/1996 |
| WO | 03057772 | 7/2003 |
| WO | 2009/080554 | 7/2009 |

* cited by examiner

STERICALLY HINDERED AMINE LIGHT STABILIZERS WITH A MIXED FUNCTIONALIZATION

This application is a Continuation of U.S. Application No. 13/879,114 (now issued as U.S. 9,550,941), which was filed on Apr. 12, 2013. Application No. 13/879,114 was a National Stage of PCT/EP2011/068059, which was filed on Oct. 17, 2011. This application is based upon and claims the benefit of priority to US Provisional Application No. 61/394,797, which was filed on Oct. 20, 2010.

The present invention relates to a specific sterically hindered amine with a mixed functionalization, to a composition containing an organic material subject to degradation induced by light, heat or oxidation and said sterically hindered amine and to the use of said sterically hindered amine for stabilizing an organic material.

The present invention relates in particular to a compound of the formula (I)

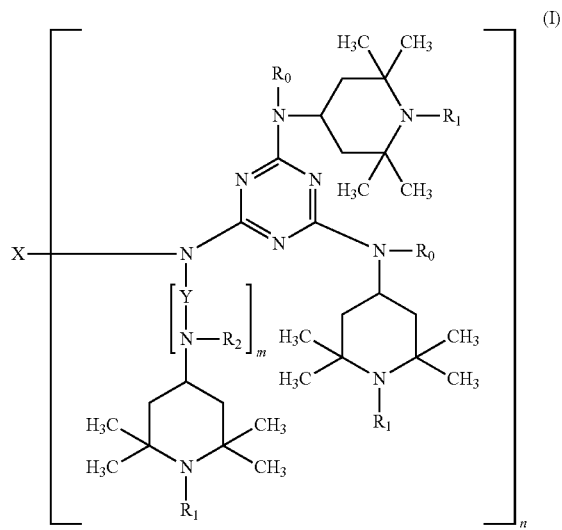

wherein
one or two radicals of the radicals $R_1$ are independently of one another $C_1$-$C_{20}$alkyloxy or $C_3$-$C_{12}$cycloalkyloxy and the remaining radicals $R_1$ are independently of one another hydrogen, $C_1$-$C_{20}$alkyl or $C_3$-$C_{12}$cycloalkyl;
the radicals $R_0$ and $R_2$ are independently of one another hydrogen, $C_1$-$C_{20}$alkyl, $C_3$-$C_{12}$cycloalkyl or a group of the formula (II-a)

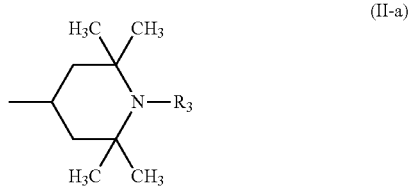

with $R_3$ being hydrogen, $C_1$-$C_{20}$alkyl, $C_3$-$C_{12}$cycloalkyl, $C_1$-$C_{20}$alkyloxy or $C_3$-$C_{12}$cycloalkyloxy;
Y is $C_2$-$C_{12}$alkylene;
m is 0 or 1;
n is 1, 2 or 3;
when n is 1, X is hydrogen, $C_1$-$C_{20}$alkyl, $C_3$-$C_{12}$cycloalkyl or a group of the formula (II-a);
when n is 2, X is $C_2$-$C_{12}$alkylene;
when n is 3, X is a group N(Z—)$_3$ with Z being $C_2$-$C_{12}$alkylene.

Examples of $C_1$-$C_{20}$alkyloxy are methoxy, ethoxy, propoxy, isopropoxy, n-butoxy, sec-butoxy, isobutoxy, tert-butoxy, 2-ethylbutoxy, n-pentyloxy, isopentyloxy, 1-methylpentyloxy, 1,3-dimethylbutoxy, n-hexyloxy, 1-methylhexyloxy, n-heptyloxy, isoheptyloxy, 1,1,3,3-tetramethylbutyloxy, 1-methylheptyloxy, 3-methylheptyloxy, n-octyloxy, 2-ethylhexyloxy, 1,1,3-trimethylhexyloxy, 1,1,3,3-tetramethylpentyloxy, nonyloxy, decyloxy, undecyloxy, 1-methylundecyloxy, dodecyloxy, 1,1,3,3,5,5-hexa-methylhexyloxy, tridecyloxy, tetradecyloxy, pentadecyloxy, hexadecyloxy, heptadecyloxy, octadecyloxy and eicosyloxy. $C_1$-$C_4$alkyloxy, in particular propoxy, is preferred.

A preferred example of $C_3$-$C_{12}$cycloalkyloxy is cyclohexyloxy.

Examples of $C_1$-$C_{20}$alkyl are methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl and eicosyl. $C_1$-$C_4$alkyl is preferred.

A preferred example of $C_3$-$C_{12}$cycloalkyl is cyclohexyl.

Examples of $C_2$-$C_{12}$alkylene are methylene, ethylene, propylene, trimethylene, tetramethylene, pentamethylene, hexamethylene, heptamethylene, octamethylene, nonamethylene, decamethylene, undecamethylene and dodecamethylene. Ethylene, trimethylene and hexamethylene are preferred.

Of interest are compounds of the formula (I) wherein
one or two radicals of the radicals $R_1$ are independently of one another $C_1$-$C_{10}$alkyloxy or $C_3$-$C_6$cycloalkyloxy and the remaining radicals $R_1$ are independently of one another hydrogen, $C_1$-$C_{10}$alkyl or $C_3$-$C_6$cycloalkyl;
the radicals $R_0$ and $R_2$ are independently of one another hydrogen, $C_1$-$C_{10}$alkyl, $C_3$-$C_6$cycloalkyl or a group of the formula (II-a);
the radicals $R_3$ are independently of one another hydrogen, $C_1$-$C_{10}$alkyl, $C_3$-$C_6$cycloalkyl, $C_1$-$C_{10}$alkyloxy or $C_3$-$C_6$cycloalkyloxy;
Y is $C_2$-$C_8$alkylene;
m is 0 or 1;
n is 1, 2 or 3;
when n is 1, X is hydrogen, $C_1$-$C_{10}$ alkyl, $C_3$-$C_6$cycloalkyl or a group of the formula (II-a);
when n is 2, X is $C_2$-$C_8$alkylene;
when n is 3, X is a group N(Z—)$_3$ with Z being $C_2$-$C_8$alkylene.

Of further interest are compounds of the formula (I) wherein
one or two radicals of the radicals $R_1$ are independently of one another $C_1$-$C_4$alkyloxy or cyclohexyloxy and the remaining radicals $R_1$ are independently of one another hydrogen, $C_1$-$C_4$alkyl or cyclohexyl;
the radicals $R_0$ and $R_2$ are independently of one another hydrogen, $C_1$-$C_4$alkyl, cyclohexyl or a group of the formula (II-a);

the radicals $R_3$ are independently of one another hydrogen, $C_1$-$C_4$alkyl, cyclohexyl, $C_1$-$C_4$alkyloxy or cyclohexyloxy;

Y is $C_2$-$C_6$alkylene;

m is 0 or 1;

n is 1, 2 or 3;

when n is 1, X is hydrogen, $C_1$-$C_4$alkyl, cyclohexyl or a group of the formula (II-a);

when n is 2, X is $C_2$-$C_6$alkylene;

when n is 3, X is a group N(Z—)$_3$ with Z being $C_2$-$C_6$alkylene.

Of particular interest are compounds of the formula (I) wherein one or two radicals of the radicals $R_1$ are independently of one another $C_1$-$C_4$alkyloxy and the remaining radicals $R_1$ are independently of one another hydrogen or $C_1$-$C_4$alkyl;

the radicals $R_0$ are independently of one another $C_1$-$C_4$alkyl or a group of the formula (II-a);

the radicals $R_3$ are independently of one another hydrogen, $C_1$-$C_4$alkyl or $C_1$-$C_4$alkyloxy;

m is 0;

n is 1, 2 or 3;

when n is 1, X is hydrogen, $C_1$-$C_4$alkyl or a group of the formula (II-a);

when n is 2, X is hexamethylene;

when n is 3, X is a group N(Z—)$_3$ with Z being ethylene.

According to a preferred embodiment of the present invention one or two radicals of the radicals $R_1$ are propoxy and the remaining radicals $R_1$ are independently of one another hydrogen or methyl.

Examples of compounds of the formula (I) are

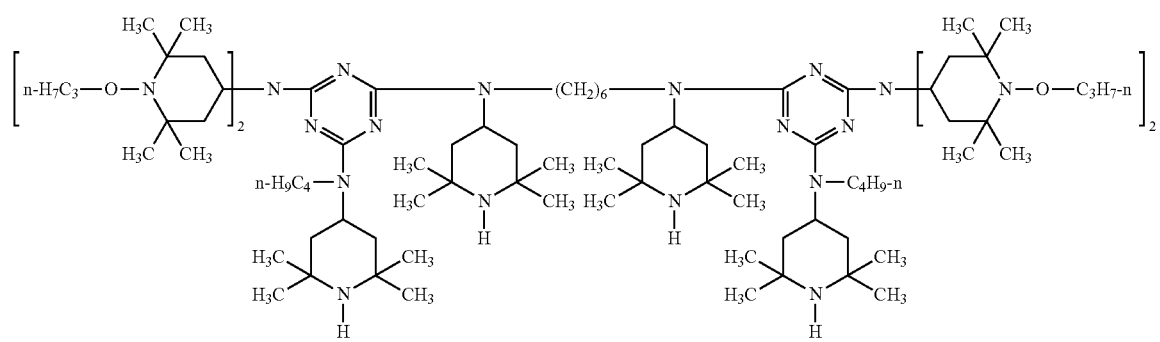
(I-4)
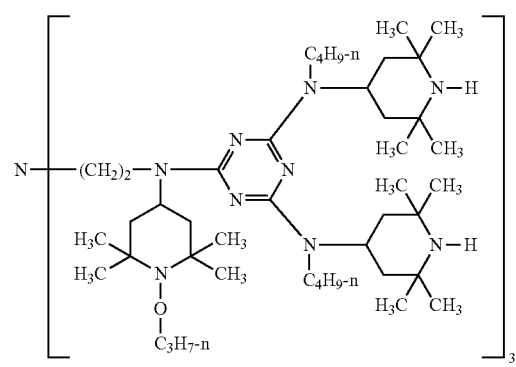
(I-5)
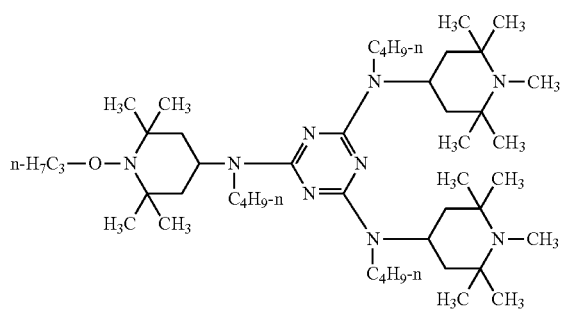
(I-6)
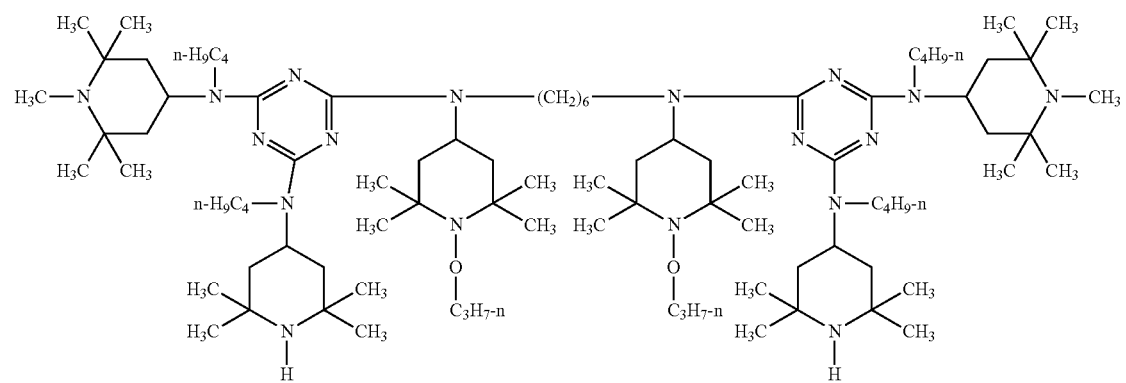
(I-7)
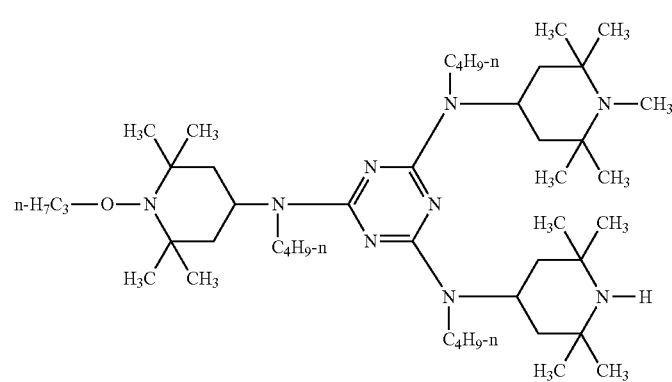
(I-8)

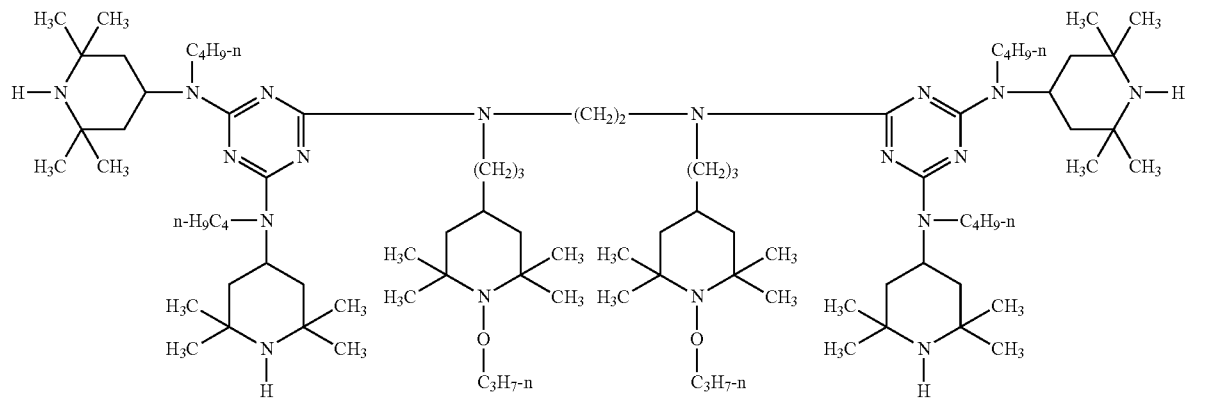

(I-9)

The compounds of the instant invention are suitable for stabilizing organic materials against degradation induced by light, heat or oxidation. Examples of such organic materials are the following:

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:
   a) radical polymerisation (normally under high pressure and at elevated temperature).
   b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylenepropylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimides, polyesterimides, polyhydantoins and polybenzimidazoles.

18. Polyesters derived from dicarboxylic acids and diols and/or from hydroxycarboxylic acids or the corresponding lactones or lactides, for example polyethylene terephthalate, polybutylene terephthalate, poly-1,4-dimethylolcyclohexane terephthalate, polyalkylene naphthalate and polyhydroxybenzoates as well as copolyether esters derived from hydroxyl-terminated polyethers, and also polyesters modified with polycarbonates or MBS. Copolyesters may comprise, for example—but are not limited to—polybutylenesuccinate/terephtalate, polybutyleneadipate/terephthalate, polytetramethyleneadipate/terephthalate, polybutylensuccinate/adipate, polybutylensuccinate/carbonate, poly-3-hydroxybutyrate/octanoate copolymer, poly-3-hydroxybutyrate/hexanoate/decanoate terpolymer. Furthermore, aliphatic polyesters may comprise, for example—but are not limited to—the class of poly(hydroxyalkanoates), in particular, poly(propiolactone), poly(butyrolactone), poly(pivalolactone), poly(valerolactone) and poly(caprolactone), polyethylenesuccinate, polypropylenesuccinate, polybutylenesuccinate, polyhexamethylenesuccinate, polyethyleneadipate, polypropyleneadipate, polybutyleneadipate, polyhexamethyleneadipate, polyethyleneoxalate, polypropyleneoxalate, polybutyleneoxalate, polyhexamethyleneoxalate, polyethylenesebacate, polypropylenesebacate, polybutylenesebacate and polylactic acid (PLA) as well as corresponding polyesters modified with polycarbonates or MBS. The term "polylactic acid (PLA)" designates a homo-polymer of preferably poly-L-lactide and any of its blends or alloys with other polymers; a co-polymer of lactic acid or lactide with other monomers, such as hydroxy-carboxylic acids, like for example glycolic acid, 3-hydroxy-butyric acid, 4-hydroxy-butyric acid, 4-hydroxy-valeric acid, 5-hydroxy-valeric acid, 6-hydroxy-caproic acid and cyclic forms thereof; the terms "lactic acid" or "lactide" include L-lactic acid, D-lactic acid, mixtures and dimers thereof, i.e. L-lactide, D-lactide, meso-lacide and any mixtures thereof.

19. Polycarbonates and polyester carbonates.

20. Polyketones.

21. Polysulfones, polyether sulfones and polyether ketones.

22. Crosslinked polymers derived from aldehydes on the one hand and phenols, ureas and melamines on the other hand, such as phenol/formaldehyde resins, urea/formaldehyde resins and melamine/formaldehyde resins.

23. Drying and non-drying alkyd resins.

24. Unsaturated polyester resins derived from copolyesters of saturated and unsaturated dicarboxylic acids with polyhydric alcohols and vinyl compounds as crosslinking agents, and also halogen-containing modifications thereof of low flammability.
25. Crosslinkable acrylic resins derived from substituted acrylates, for example epoxy acrylates, urethane acrylates or polyester acrylates.
26. Alkyd resins, polyester resins and acrylate resins crosslinked with melamine resins, urea resins, isocyanates, isocyanurates, polyisocyanates or epoxy resins.
27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.
28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
29. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.
30. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
31. Aqueous emulsions of natural or synthetic rubber, e.g. natural latex or latices of carboxylated styrene/butadiene copolymers.

Preferred organic materials are:
1) Homo and copolymers of olefin monomers such as ethylene and propylene, but also higher 1-olefins such as 1-butene, 1-pentene, 1-hexene or 1-octene. Preferred is polyethylene LDPE and LLDPE, HDPE and polypropylene.
2) Homo- and copolymers of olefin monomers with diolefin monomers such as butadiene, isoprene and cyclic olefins such as norbornene.
3) Copolymers of one ore more 1-olefins and/or diolefins with carbon monoxide and/or with other vinyl monomers, including, but not limited to vinyl acetate, vinyl ketone, styrene, maleic acid anhydride and vinyl chloride.
4) Polyvinyl alcohol.
5) Other thermoplastics such as polystyrene, styrene-acrylonitrile copolymer, acrylonitrile-butadiene-styrene copolymer, polyvinyl chloride, polyvinylidene chloride, polyvinyl acetate, polyvinylbutyral, ethylene-vinyl alcohol copolymer, polyethylene terephthalate (PET), polybutylene terephthalate (PBT), liquid crystal polyesters (LCP's), polyacetals (e.g., POM), polyamides (PA), polycarbonates, polyurethane and polyphenylene sulfide (PPS); polymer blends or polymer alloys formed of two or more of these resins; and compounds obtained by adding fillers such as glass fibers, carbon fibers, semi-carbonized fibers, cellulose fibers and glass beads, flame retardants, blowing agents, antimicrobial agents, crosslinking agents, fine polyolefin resin powder, polyolefin waxes, ethylene bisamide waxes, metallic soaps and the like either singly or in combination to these resins. Examples of thermosetting resins, on the other hand, can include thermosetting resins such as epoxy resins, melamine resins and unsaturated polyester resins; and compounds obtained by incorporating fillers such as glass fibers, carbon fibers, semi-carbonized fibers, cellulose fibers and glass beads, flame retardants and the like either singly or in combination to these resins.

Further preferred organic materials are:
Biodegradable polymers of either natural or synthetic origin including but not limited to polyethylensuccinate, polybutylensuccinate, polybutylensuccinate/adipate, polybutylensuccinate/carbonate, polybutylensuccinate/terephtalate, polycaprolactone, poly(hydroxyalkanoates), poly 3-hydroxybutyrate, polylactic acid, polyester amides, or blends of these materials with natural or modified starch, polysaccharides, lignin, wood flour, cellulose or chitin.

Another embodiment of the present invention is a composition comprising (A) an organic material subject to degradation induced by light, heat or oxidation and (B) a compound of the formula (I) as described above, as well as the method for stabilizing the organic material.

The organic material is preferably a thermoplastic natural or synthetic polymer, in particular from one of the above groups. A polyolefin homo- or copolymer, a starch modified polyolefin or a starch based polymer composite is preferred and a polyethylene, a polypropylene, a polyethylene copolymer or a polypropylene copolymer is particularly preferred.

In general, the composition may additionally contain one, two or more conventional additives which are either commercially available or can be prepared according to known methods. Examples of said conventional additives are listed below.

1. Antioxidants
1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1-yl)phenol and mixtures thereof.
1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol.
1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.
1.4. Tocopherols, for example α-tocopherol, β-tocopherol, γ-tocopherol, δ-tocopherol and mixtures thereof (vitamin E).
1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulfide.
1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α- methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxy-phenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]undecane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl)propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'- dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazine, N,N,N',N'-tetraphenyl-1,4-diaminobut-2-ene.

2. UV Absorbers and Light Stabilizers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-($\alpha,\alpha$-dimethylbenzyl)-2'-hydroxyphenyl)benzotriazole, 2-(3'-tert-butyl-2'-hydroxy-5'-(2-octyloxycarbonylethyl) phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$, where R=3'-tert-butyl-4'-hydroxy-5'-2H-benzotriazol-2-ylphenyl, 2-[2'-hydroxy-3'-($\alpha,\alpha$-dimethyl benzyl)-5'-(1,1,3,3-tetramethylbutyl)-phenyl] benzotriazole; 2-[2'-hydroxy-3'-(1,1,3,3-tetramethylbutyl)-5'-($\alpha,\alpha$-dimethylbenzyl)-phenyl] benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl $\alpha$-cyano-$\beta,\beta$-diphenylacrylate, isooctyl $\alpha$-cyano-$\beta,\beta$-diphenylacrylate, methyl $\alpha$-carbomethoxycinnamate, methyl $\alpha$-cyano-$\beta$-methyl-p-methoxycinnamate, butyl $\alpha$-cyano-$\beta$-methyl-p-methoxycinnamate, methyl $\alpha$-carbomethoxy-p-methoxycinnamate, N-($\beta$-carbomethoxy-$\beta$-cyanovinyl)-2-methylindoline, neopentyl tetra($\alpha$-cyano-$\beta,\beta$-diphenylacrylate.

2.5. Nickel compounds, for example nickel complexes of 2,2'-thio-bis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example carbonic acid bis(1-undecyloxy-2,2,6,6-tetramethyl-4-piperidyl)ester, bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl) hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino) ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl) hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-$\alpha$-olefin copolymer with 2,2,6,6-tetramethyl-4-aminopiperidine or 1,2,2,6,6-pentamethyl-4-aminopiperidine, 2,4-bis[N-(1-cyclohexyloxy-2,2,6,6-tetramethylpiperidine-4-yl)-N-butylamino]-6-(2-hydroxyethyl)amino-1,3,5-triazine, 1-(2-hydroxy-2-methylpropoxy)-4-octadecanoyloxy-2,2,6,6- tetramethylpiperidine, 5-(2-ethylhexanoyl)oxymethyl-3,3,5-trimethyl-2-morpholinone, Sanduvor (Clariant; CAS Reg. No. 106917-31-1], 5-(2-ethylhexanoyl)oxymethyl-3,3,5-trimethyl-2-morpholinone, the reaction product of 2,4-bis[(1-cyclohexyloxy-2,2,6,6-piperidine-4-yl)butylamino]-6-chloro-s-triazine with N,N'-bis(3-aminopropyl)ethylenediamine), 1,3,5-tris(N-cyclohexyl-N-(2,2,6,6-tetramethylpiperazine-3-one-4-yl)amino)-s-triazine, 1,3,5-tris(N-cyclohexyl-N-(1,2,2,6,6-pentamethylpiperazine-3-one-4-yl)amino)-s-triazine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{hydroxy-4-[3-(2-ethylhexyl-1-oxy)-2-hydroxypropyloxy]phenyl}-4,6-bis(2,4-dimethylphenyl)-1,3,5-triazine, 2,4-bis(4-[2-ethylhexyloxy]-2-hydroxyphenyl)-6-(4-methoxyphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl)hydrazine, 3-salicyloylamino-1,2,4-triazole, bis(benzylidene)oxalyl di hydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecyl pentaerythritol di phosphite, bis(2,4-di-tert-butylphenyl)pentaerythritol diphosphite, bis(2,4-di-cumylphenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl)methyl phosphite, bis(2,4-di-tert-butyl-6-methylphenyl)ethyl phosphite, 6-fluoro-2,4,8,10-tetra-tert-butyl-12-methyl-dibenz[d,g]-1,3,2-dioxaphosphocin, 2,2',2''-nitrilo[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

The following phosphites are especially preferred:

Tris(2,4-di-tert-butylphenyl) phosphite (Irgafos®168, Ciba Specialty Chemicals Inc.), tris(nonylphenyl) phosphite,

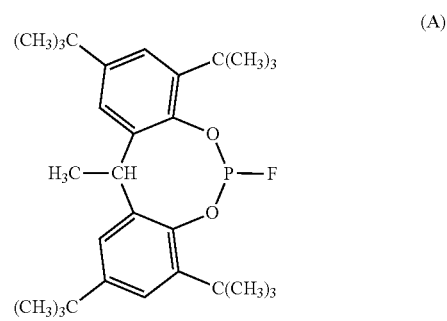

(A)

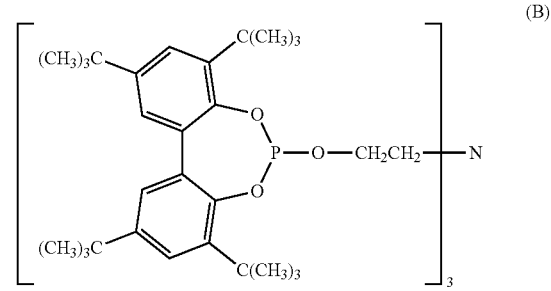

(B)

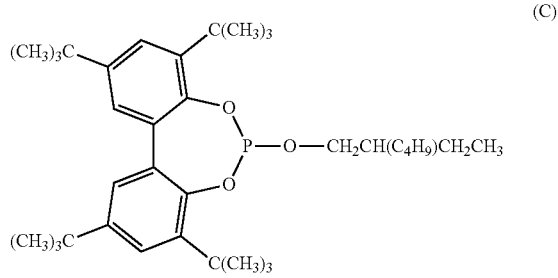

(C)

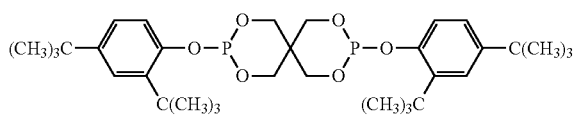

(D)

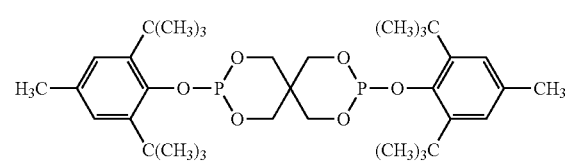

(E)

(F)

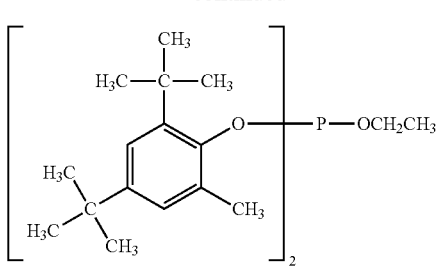

(G)

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-heptadecylnitrone, N-octadecyl-alpha-hexadecylnitrone, nitrone derived from N,N-dialkylhydroxylamine derived from hydrogenated tallow amine.

7. Thiosynergists, for example dilauryl thiodipropionate, dimistryl thiodipropionate, distearyl thiodipropionate or distearyl disulfide.

8. Peroxide scavengers, for example esters of p-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilizers, for example copper salts in combination with iodides and/or phosphorus compounds and salts of divalent manganese.

10. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyldibenzylidene)sorbitol, and 1,3:2,4-di(benzylidene)sorbitol.

12. Fillers and reinforcing agents, for example calcium carbonate, silicates, glass fibres, glass beads, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839, EP-A-0591102; EP-A-1291384 or 3-[4-(2-acetoxyethoxy)phenyl]-5,7-di-tert-butylbenzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one, 3-(2-acetyl-5-isooctylphenyl)-5-isooctylbenzofuran-2-one.

The weight ratio of component (B) to the conventional additive is preferably 1:100 to 100:1, preferably 1:50 to 50:1, for example 1:20 to 20:1 or 1:5 to 5:1.

Preferred conventional additives are:

1) Fillers and reinforcing agents such as calcium carbonate, silicas, glass fibres, glass bulbs, talc, kaolin, mica, barium sulfate, metal oxides and hydroxides, carbon black, graphite, wood flour, flours of other natural products, synthetic fibers, stearates used as fillers such as calcium stearate on zinc stearate.

2) Pigments such as carbon black, titanium dioxide in its rutile or anatase forms, and other colour pigments.

3) UV absorbers.

4) Conventional hindered amine light stabilizers.

5) Processing additives such as antislip/antiblock additives, plasticizers, optical brighteners, antistatic agents and blowing agents.

6) Antioxidants.

7) Terpene derivatives such as the ones included in the comprehensive list of Kirk-Othmer, Encyclopedia of Chemical Technology, John Wiley & Sons, 4. ed. (1994), Vol. 23, p. 833-882 and in WO 03/080011.

Thus, a further preferred embodiment of the present invention relates to a composition as defined above which contains in addition one, two or more of the following components (C-I) a filler or reinforcing agent,
(C-II) a pigment,
(C-III) a further light stabilizer,
(C-IV) a processing additive,
(C-V) an antioxidant,
(C-VI) a terpene derivative.

The components (B) and optionally (C-I) to (C-VI) can be incorporated into the organic material to be stabilized by known methods, for example before or during shaping or by applying the dissolved or dispersed compounds to the organic material, if necessary with subsequent evaporation of the solvent. The components can be added to the organic material in the form of a powder, granules or a masterbatch, which contains these components in, for example, a concentration of from 2.5 to 25% by weight.

If desired, the components (B) and optionally (C-I) to (C-VI) can be melt blended with each other before incorporation in the organic material. They can be added to a polymer before or during the polymerization or before the crosslinking.

Component (B) is preferably present in the organic material to be stabilized (component (A)) in an amount of 0.01 to 10%, preferably 0.05 to 5%, relative to the weight of component (A).

Component (C-I) is preferably present in the organic material to be stabilized (component (A)) in an amount of 0.1 to 20%, preferably 0.5 to 10%, relative to the weight of component (A).

Component (C-II) is preferably present in the organic material to be stabilized (component (A)) in an amount of 0.01 to 10%, preferably 0.05 to 5%, relative to the weight of component (A).

Component (C-III) is preferably present in the organic material to be stabilized (component (A)) in an amount of 0.01 to 10%, preferably 0.05 to 9%, relative to the weight of component (A).

Component (C-IV) is preferably present in the organic material to be stabilized (component (A)) in an amount of 0.01 to 9%, preferably 0.05 to 3%, relative to the weight of component (A).

Component (C-V) is preferably present in the organic material to be stabilized (component (A)) in an amount of 0.01 to 9%, preferably 0.05 to 3%, relative to the weight of component (A).

Component (C-VI) is preferably present in the organic material to be stabilized (component (A)) in an amount of 0.01 to 10%, preferably 0.09 to 5%, relative to the weight of component (A).

The compositions according to the present invention can be advantageously used for the preparation of various shaped articles. Examples are:

I-1) Floating devices, marine applications, pontoons, buoys, plastic lumber for decks, piers, boats, kayaks, oars, and beach reinforcements.

I-2) Automotive applications, in particular bumpers, dashboards, battery, rear and front linings, moldings parts under the hood, hat shelf, trunk linings, interior linings, air bag covers, electronic moldings for fittings (lights), panes for dashboards, headlamp glass, instrument panel, exterior linings, upholstery, automotive lights, head lights, parking lights, rear lights, stop lights, interior and exterior trims; door panels; gas tank; glazing front side; rear windows; seat backing, exterior panels, wire insulation, profile extrusion for sealing, cladding, pillar covers, chassis parts, exhaust systems, fuel filter/filler, fuel pumps, fuel tank, body side mouldings, convertible tops, exterior mirrors, exterior trim, fasteners/fixings, front end module, glass, hinges, lock systems, luggage/roof racks, pressed/stamped parts, seals, side impact protection, sound deadener/insulator and sunroof.

I-3) Road traffic devices, in particular sign postings, posts for road marking, car accessories, warning triangles, medical cases, helmets, tires.

I-4) Devices for plane, railway, motor car (car, motorbike) including furnishings.

I-5) Devices for space applications, in particular rockets and satellites, e.g. reentry shields.

I-6) Devices for architecture and design, mining applications, acoustic quietized systems, street refuges, and shelters.

II-1) Appliances, cases and coverings in general and electric/electronic devices (personal computer, telephone, portable phone, printer, television-sets, audio and video devices), flower pots, satellite TV bowl, and panel devices.

II-2) Jacketing for other materials such as steel or textiles.

II-3) Devices for the electronic industry, in particular insulation for plugs, especially computer plugs, cases for electric and electronic parts, printed boards, and materials for electronic data storage such as chips, check cards or credit cards.

II-4) Electric appliances, in particular washing machines, tumblers, ovens (microwave oven), dish-washers, mixers, and irons.

II-5) Covers for lights (e.g. street-lights, lamp-shades).

II-6) Applications in wire and cable (semi-conductor, insulation and cable-jacketing).

II-7) Foils for condensers, refrigerators, heating devices, air conditioners, encapsulating of electronics, semi-conductors, coffee machines, and vacuum cleaners.

III-1) Technical articles such as cogwheel (gear), slide fittings, spacers, screws, bolts, handles, and knobs.

III-2) Rotor blades, ventilators and windmill vanes, solar devices, swimming pools, swimming pool covers, pool liners, pond liners, closets, wardrobes, dividing walls, slat walls, folding walls, roofs, shutters (e.g. roller shutters), fittings, connections between pipes, sleeves, and conveyor belts.

III-3) Sanitary articles, in particular shower cubicles, lavatory seats, covers, and sinks.

III-4) Hygienic articles, in particular diapers (babies, adult incontinence), feminine hygiene articles, shower curtains, brushes, mats, tubs, mobile toilets, tooth brushes, and bed pans.

III-5) Pipes (cross-linked or not) for water, waste water and chemicals, pipes for wire and cable protection, pipes for gas, oil and sewage, guttering, down pipes, and drainage systems.

III-6) Profiles of any geometry (window panes) and siding.

III-7) Glass substitutes, in particular extruded plates, glazing for buildings (monolithic, twin or multiwall), aircraft, schools, extruded sheets, window film for architectural glazing, train, transportation, sanitary articles, and greenhouse.

III-8) Plates (walls, cutting board), extrusion-coating (photographic paper, tetrapack and pipe coating), silos, wood substitute, plastic lumber, wood composites, walls, surfaces, furniture, decorative foil, floor coverings (interior and exterior applications), flooring, duck boards, and tiles.

III-9) Intake and outlet manifolds.

III-10) Cement-, concrete-, composite-applications and covers, siding and cladding, hand rails, banisters, kitchen work tops, roofing, roofing sheets, tiles, and tarpaulins.

IV-1) Plates (walls and cutting board), trays, artificial grass, astroturf, artificial covering for stadium rings (athletics), artificial floor for stadium rings (athletics), and tapes.

IV-2) Woven fabrics continuous and staple, fibers (carpets/hygienic articles/geotextiles/monofilaments; filters; wipes/curtains (shades)/medical applications), bulk fibers (applications such as gown/protection clothes), nets, ropes, cables, strings, cords, threads, safety seat-belts, clothes, underwear, gloves; boots; rubber boots, intimate apparel, garments, swimwear, sportswear, umbrellas (parasol, sunshade), parachutes, paraglides, sails, "balloon-silk", camping articles, tents, airbeds, sun beds, bulk bags, and bags.

IV-3) Membranes, insulation, covers and seals for roofs, tunnels, dumps, ponds, dumps, walls roofing membranes, geomembranes, swimming pools, curtains (shades)/sunshields, awnings, canopies, wallpaper, food packing and wrapping (flexible and solid), medical packaging (flexible & solid), airbags/safety belts, arm- and head rests, carpets, centre console, dashboard, cockpits, door, overhead console module, door trim, headliners, interior lighting, interior mirrors, parcel shelf, rear luggage cover, seats, steering column, steering wheel, textiles, and trunk trim.

V) Films (packaging, dump, laminating, agriculture and horticulture, greenhouse, mulch, tunnel, silage), bale wrap, swimming pools, waste bags, wallpaper, stretch film, raffia, desalination film, batteries, and connectors.

VI-1) Food packing and wrapping (flexible and solid), BOPP, BOPET, bottles.

VI-2) Storage systems such as boxes (crates), luggage, chest, household boxes, pallets, shelves, tracks, screw boxes, packs, and cans.

VI-3) Cartridges, syringes, medical applications, containers for any transportation, waste baskets and waste bins, waste bags, bins, dust bins, bin liners, wheely bins, container in general, tanks for water/used water/chemistry/gas/oil/gasoline/diesel; tank liners, boxes, crates, battery cases, troughs, medical devices such as piston, ophthalmic applications, diagnostic devices, and packing for pharmaceuticals blister.

VII-1) Extrusion coating (photo paper, tetrapack, pipe coating), household articles of any kind (e.g. appliances, thermos bottle/clothes hanger), fastening systems such as plugs, wire and cable clamps, zippers, closures, locks, and snap-closures.

VII-2) Support devices, articles for the leisure time such as sports and fitness devices, gymnastics mats, ski-boots, inline-skates, skis, big foot, athletic surfaces (e.g. tennis grounds); screw tops, tops and stoppers for bottles, and cans.

VII-3) Furniture in general, foamed articles (cushions, impact absorbers), foams, sponges, dish clothes, mats, garden chairs, stadium seats, tables, couches, toys, building kits (boards/figures/balls), playhouses, slides, and play vehicles.

VII-4) Materials for optical and magnetic data storage.

VII-5) Kitchen ware (eating, drinking, cooking, storing).

VII-6) Boxes for CD's, cassettes and video tapes; DVD electronic articles, office supplies of any kind (ball-point pens, stamps and ink-pads, mouse, shelves, tracks), bottles of any volume and content (drinks, detergents, cosmetics including perfumes), and adhesive tapes.

VII-7) Footwear (shoes/shoe-soles), insoles, spats, adhesives, structural adhesives, food boxes (fruit, vegetables, meat, fish), synthetic paper, labels for bottles, couches, artificial joints (human), printing plates (flexographic), printed circuit boards, and display technologies.

VII-8) Devices of filled polymers (talc, chalk, china clay (kaolin), wollastonite, pigments, carbon black, $TiO_2$, mica, nanocomposites, dolomite, silicates, glass, asbestos).

The compounds of the present invention are excellent stabilizers against the harmful effect of light and heat in different applications like, but not limited to agriculture, with or without the use of pesticides, automotive and/or flame retardant applications.

The following articles which need stabilization in natural sunlight and/or humidity at low, ambient or elevated temperature relate to a further embodiment of the present invention: Plastic films, sheets, bags, bottles, styrofoam cups, plates, utensils, blister packages, boxes, package wrappings, plastic fibers, tapes, agricultural articles such as twine agricultural films, mulch films, small tunnel films, banana bags, direct covers, nonwoven, pots for agricultural use, goetextiles, landfill covers, industrial covers, waste covers, temporary scaffolding sheets, building films, silt fences, poultry curtains, films for building temporary shelter constructions, disposable diapers, disposable garments, and the like. The articles may be manufactured by any process available to those of ordinary skill in the art including, but not limited to extrusion, extrusion blowing, film casting, film blowing, calendering, injection molding, blow molding, compression molding, thermoforming, spinning, blow extrusion and rotational casting.

A further preferred embodiment of the present invention is a shaped article, preferably a film fiber, profile, pipe, bottle, tank or container, made of a composition as defined above. A mulch film is particularly preferred.

Unless indicated otherwise, heretofore and hereinafter, all parts and percentages are by weight and all temperatures are given in degrees Celsius (° C.). In the following synthesis all reactions are carried out in nitrogen atmosphere except when otherwise stated.

The starting materials are known and can be prepared in analogy to known methods. Some examples are listed below.

(A) 1-n-Propoxy-2,2,6,6-tetramethyl-4-(butylamino)piperidine can be prepared e.g. in analogy to the method described in WO-A-2008/003,602, page 19.

(B) N,N'-Bis[2,2,6,6-tetramethyl-4-piperidyl]-N,N'-bis[2-(N-(2,2,6,6,-tetramethyl-4-piperidyl)-butylamino)-4-chloro-1,3,5-triazin-6-yl]hexamethylene-1,6-diamine of the formula

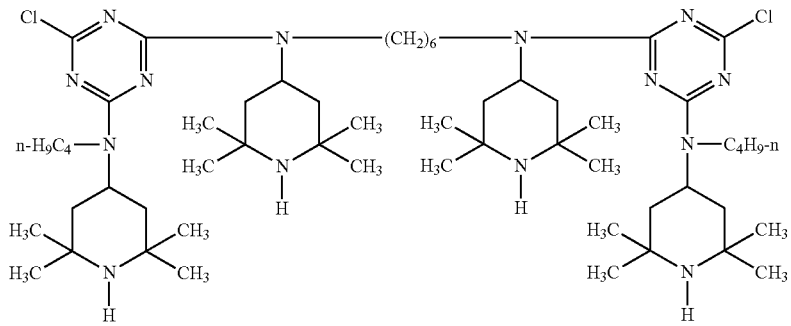

can be prepared e.g. in analogy to the method described in CA-C-2,191,832.

(C) 2,4-Bis[N-(1-n-propoxy-2,2,6,6-tetramethylpiperidin-4-yl)-n-butylamino]-6-chloro-1,3,5-triazine of the formula

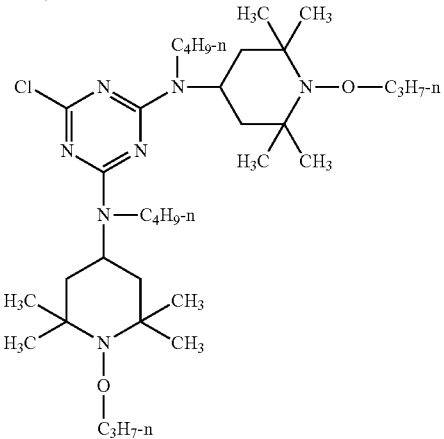

can be prepared e.g. in analogy to the method described in U.S. Pat. No. 6,117,995.

(D) 2,4-Bis[N-(2,2,6,6-tetramethylpiperidin-4-yl)-n-butylamino]-6-chloro-1,3,5-triazine of the formula

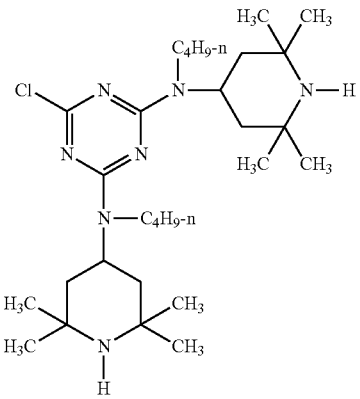

can be prepared e.g. in analogy to the method described in WO-A-1998/054,175.

(E) N,N'-bis[1-n-propoxy-2,2,6,6-tetramethylpiperidin-4-yl]hexane-1,6-diamine of the formula

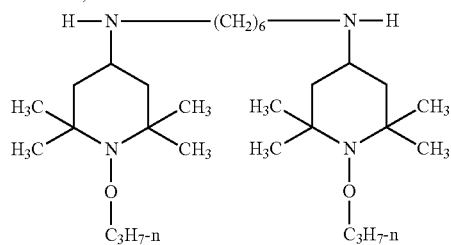

can be prepared e.g. in analogy to the method described in WO-A-2008/003,605.

(F) 2-[N-(2,2,6,6-tetramethylpiperidin-4-yl)-n-butylamino]-4,6-dichloro-1,3,5-triazine of the formula

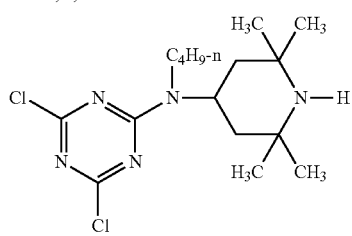

can be prepared e.g. in analogy to the method described in WO-A-1998/054,175.

(G) 2,4-Bis[N-(1,2,2,6,6-pentamethylpiperidin-4-yl)-n-butylamino]-6-chloro-1,3,5-triazine of the formula

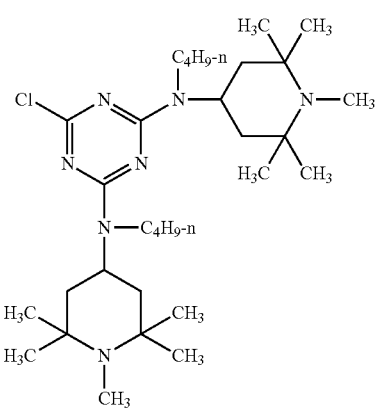

can be prepared e.g. in analogy to the method described in WO-A-1998/054,175.

EXAMPLE 1

Preparation Of The Compound Of The Formula (I-1)

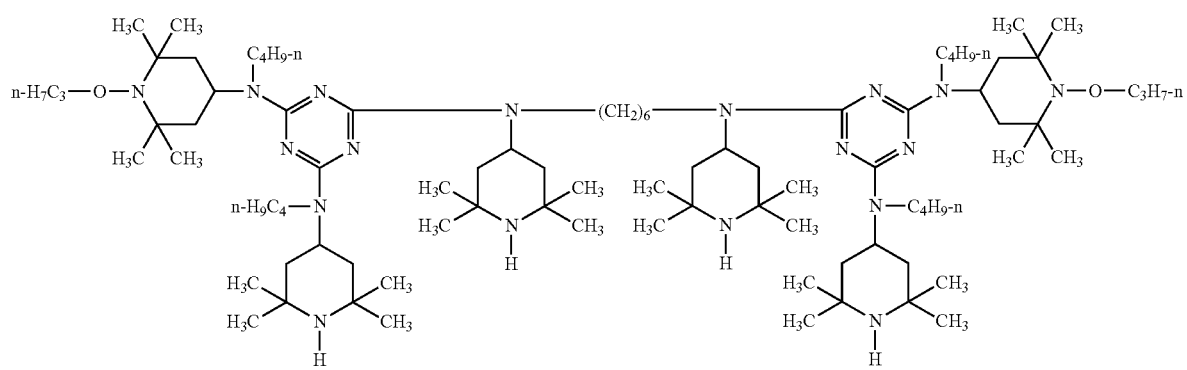

A four-necked round-bottom flask equipped with a mechanical stirrer, thermocouple, dropping funnel and condenser is charged with 45.0 g of N,N'-bis[2,2,6,6-tetramethyl-4-piperidyl]-N,N'-bis[2-(N-(2,2,6,6,-tetramethyl-4-piperidyl)-butylamino-4-chloro-1,3,5-triazin-6-yl] hexamethylene-1,6-diamine dissolved in 200 ml of mesitylene. 23.35 g of 1-n-propoxy-2,2,6,6-tetramethyl-4-(butylamino)piperidine are added at room temperature. NaOH (30%) is also added and the mixture is heated at reflux for 20 hours under removal of water. The solution is then cooled at room temperature and washed with water until pH=7. The solvent is removed and the product is dissolved in 10 ml of $CH_2Cl_2$ and is subsequently precipitated from cold MeOH as a white powder.

Yield: 57.1 g (87% of theory)

TGA (Thermographic Analysis; Air, 10° C./min): 120° C.: −0.19%; 255° C.: −1.70%

Elemental analysis: C: 69.05% (98.7%); H: 11.25% (100.3%); N: 16.43% (98.3%); O: 2.14% (100.9%)

ESI-MS (Electrospray ionization mass spectrometry; direct Injection): [M+H]$^+$: 1510.8 Melting point: 90-107° C.

EXAMPLE 2

Preparation Of The Compound Of The Formula (I-2)

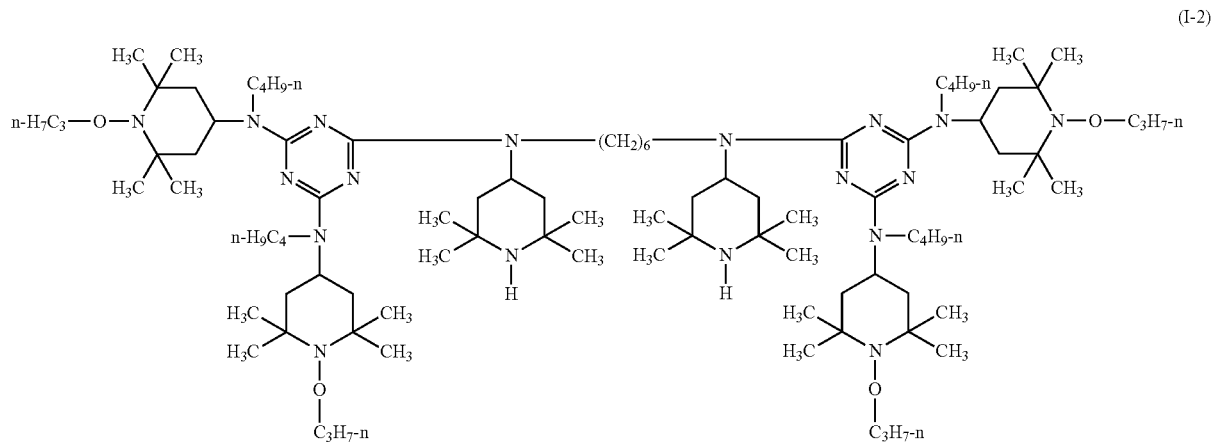

A four-necked round-bottom flask equipped with a mechanical stirrer, thermocouple, dropping funnel and condenser is charged with 7.6 g of N,N'-bis[2,2,6,6-tetramethylpiperidin-4-yl]hexane-1,6-diamine, 25.0 g of 2,4-Bis[N-(1-n-propoxy-2,2,6,6-tetramethylpiperidin-4-yl)-n-butylamino]-6-chloro-1,3,5-triazine and 19 ml of NaOH (30%) dissolved in 120 ml of xylene. The reaction is heated at reflux for 20 hours and the water is removed. Then, the reaction is cooled down at room temperature and washed with water at 60° C. until pH=7. The solvent is removed and the final brown-yellow solid is dissolved in 8.0 ml of CH$_2$Cl$_2$. The product is precipitated as white powder from 70 ml of cold MeOH.

Yield: 13.0 g (41% of theory)

TGA (Air, 10° C./min.): 210° C.: −1.01%; 260° C.: −1.55%; 300° C.: −3.02%

Elemental Analysis: C: 68.76% (99.1%); H: 11.15% (100.0%); N: 15.21% (98.1%); O: 3.82% (97.7%)

ESI-MS (Direct Injection), m/z: [M+H]$^+$: 1626.8

Melting point: 244-249° C.

EXAMPLE 3

Preparation Of The Compound Of The Formula (I-3)

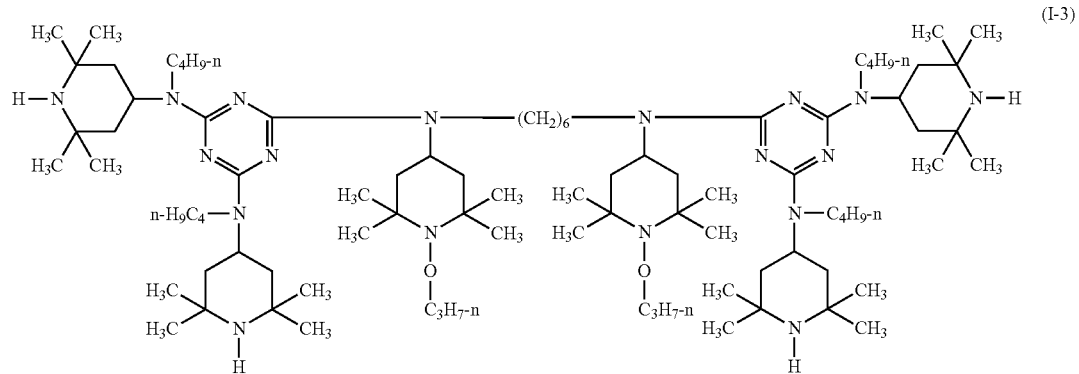

A four-necked round-bottom flask equipped with a mechanical stirrer, thermocouple, dropping funnel and condenser is charged with 100 g of 2,4-bis[N-(2,2,6,6-tetramethylpiperidin-4-yl)-n-butylamino]-6-chloro-1,3,5-triazine, 47.6 g of N,N'-bis[1-n-propoxy-2,2,6,6-tetramethylpiperidin-4-yl]hexane-1,6-diamine and 3.0 g (10 ml) of NaOH (30%) dissolved in 80 ml of xylene. The reaction is heated at reflux overnight and the water is removed. The reaction is then cooled down at room temperature and washed with water at 60° C. until pH=7. The solvent is removed under reduced pressure and a yellowish solid is obtained. The yellow solid is suspended in 100 ml of $CH_3CN$, is sonicated for 5 minutes and is stirred for 20 minutes at room temperature. The solid is then filtered, re-suspended in 30 ml of cold MeOH and is filtered again to give a white powder.

Yield: 84 g (59.8% of theory)

TGA (Air, 10° C./min.): 210° C.: −0.07%; 260° C.: −0.45%; 300° C.: −5.76%

Elemental Analysis: C: 69.59% (99.5%); N: 16.57% (99.5%); H: 11.13% (99.3%); O: 2.08% (98.1%)

ESI-MS (Direct Injection): [M+H]$^+$: 1510.9

Melting point: 155-164° C.

EXAMPLE 4

Preparation Of The Compound Of The Formula (I-4)

575 g of grey crystals are obtained. The crude product is re-crystallized from 500 ml of methanol. The desired product is obtained as colorless crystals.

Yield: 860 g (68.7% of theory)

Elemental Analysis: C: 70.12% (100.1%); H: 11.95% (99.6%); N: 10.19% (99.8%); O: 7.80% (100.4%)

ESI-MS (Direct Injection, APCI, $CH_2Cl_2$/MeOH): [M+H]$^+$: 412

Melting point: 67-69° C.

4B) Preparation of the Intermediate of the Formula

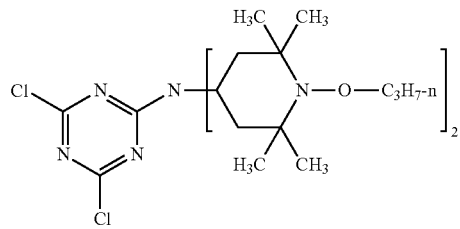

A four-necked round-bottom flask equipped with a mechanical stirrer, thermocouple, dropping funnel and condenser is charged with 8.96 g of cyanuric chloride which is dissolved in 60 ml of dichloroethane. The solution is cooled down at −10° C. and 20 g of bis[1-n-propoxy-2,2,6,6-tetramethylpiperidin-4-yl]amine dissolved in 40 ml of

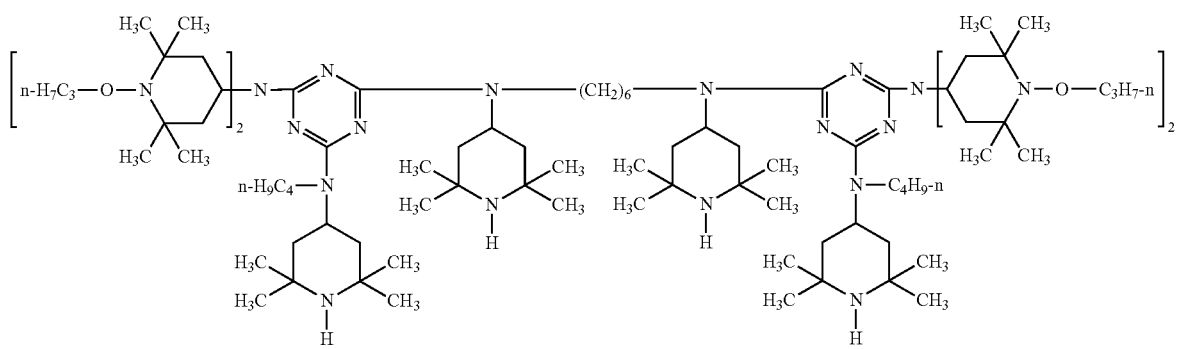

(I-4)

4A) Preparation of the Intermediate of the Formula

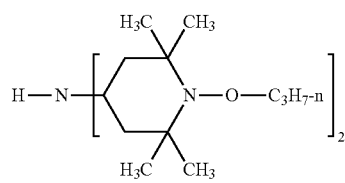

In a 2000 ml autoclave 600 g of 1-n-propoxy-2,2,6,6-tetramethylpiperidin-4-one in 1000 ml of methanol are slowly added to 230 ml of methanolic ammonia (10% solution in methanol) and 12 g of Pt-catalyst (5% on C). The mixture is heated at 60° C. under a $H_2$ pressure of 10 bar for 16 h. After the further addition of 12 g of Pt-catalyst and 50 g of 1-propoxy-2,2,6,6-tetramethylpiperidin-4-one the mixture is hydrogenated for further 21 hours under a pressure of 10 bar. After filtration of the catalyst and solvent evaporation dichloroethane is slowly added keeping the temperature below −5° C. The yellow mixture is stirred for additional 90 minutes at this temperature, then wormed up at room temperature and stirred for additional 2 hours. The reaction is again cooled down at −5° C. and 6.8 ml of NaOH (30%) is added drop wise. The reaction is stirred at room temperature overnight. 50 ml of water is added and the mixture is stirred for 2 hours. The obtained suspension is filtered to give a white solid which is washed with 20 ml of cold dichloroethane and 60 ml of water. The desired product is obtained as a white powder which is dried in an oven under vacuum at 70° C.

Yield: 20.0 g (73% of theory)

TGA (Air, 10° C./min.): 200° C.: −0.89%; 260° C.: −4.83%

LC-MS (Liquid chromatography-Mass spectrometry): [M+H]$^+$: 561

Melting point: 207-211° C.

4C) Preparation of the Intermediate of the Formula

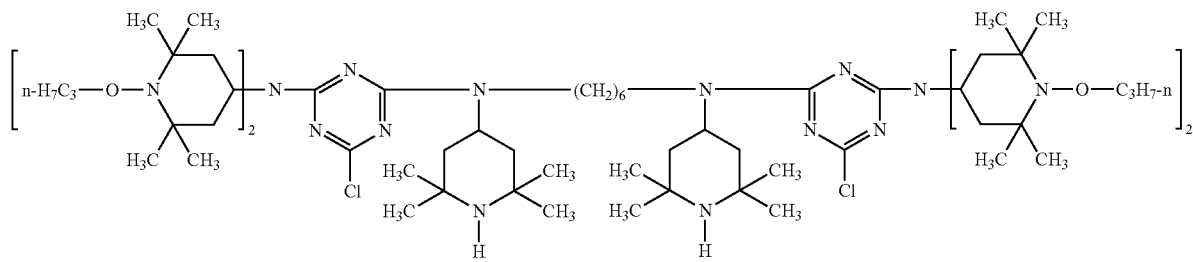

A four-necked round-bottom flask equipped with a mechanical stirrer, thermocouple, dropping funnel and condenser is charged with 19.96 g of the intermediate described under 4B, 7.03 g of N,N'-bis(2,2,6,6-tetramethypiperidin-4-yl)hexane-1,6-diamine and 7.1 ml of NaOH (30%) dissolved in 65 ml of toluene. The solution is heated at 80° C. for 8 hours. The solvent is removed and the white viscous gel dissolved in 300 ml of CH$_2$Cl$_2$. This solution is washed twice with 2×150 ml of H$_2$O. Then, the organic solvent is removed to give a white wax which is stirred in 150 ml of MeOH at 5° C. for 30 minutes. The white solid is filtered off and dried in an oven under vacuum at 70° C.

Yield: 12.5 g (48% of theory)

TGA (Air, 10° C./min.): 210° C.: −0.41%; 255° C.: −2.95%

Elemental analysis: C: 63.71% (98.1%); H: 10.12% (100.5%); N: 15.28% (98.3%); O: 4.46% (100.5%)

ESI-MS (Direct Injection, APCI, CH$_2$Cl$_2$/MeOH): [M+H]$^+$: 1442

Melting point: 208-226° C.

4D) Preparation of the Compound of the Formula (I-4)

A four-necked round-bottom flask equipped with a mechanical stirrer, thermocouple, dropping funnel and condenser is charged with 12.45 g of the intermediate described under 4C, 3.70 g of N-(2,2,6,6-tetramethylpiperidin-4-yl)-n-butylamine, 4.0 ml of NaOH (30%) dissolved in 35 m of xylene. The mixture is heated at reflux for 20 hours and the water is removed. The mixture is cooled down and washed several times with H$_2$O until pH=7. The organic solvent is removed at a rotavapor and the obtained brown solid is dissolved in 5 ml of CH$_2$Cl$_2$. The desired product is obtained as a white precipitate by adding this solution to 60 ml of cold MeOH.

Yield: 12.5 g (76% of theory)

TGA (Air, 10° C./min): 195° C.: −0.17%; 255° C.: −0.96%

Elemental Analysis: C: 69.74% (100.1%); H: 11.01% (98.9%); N: 15.82% (101.1%); O: 3.59% (100.5%)

ESI-MS (Direct Injection, APCI, CH$_2$Cl$_2$/MeOH): [M+H]$^+$: 1794

Melting point (m.p.): m.p.1: 203-206° C.; m.p.2: 235-242° C.

EXAMPLE 5

Preparation Of The Compound Of The Formula (I-5)

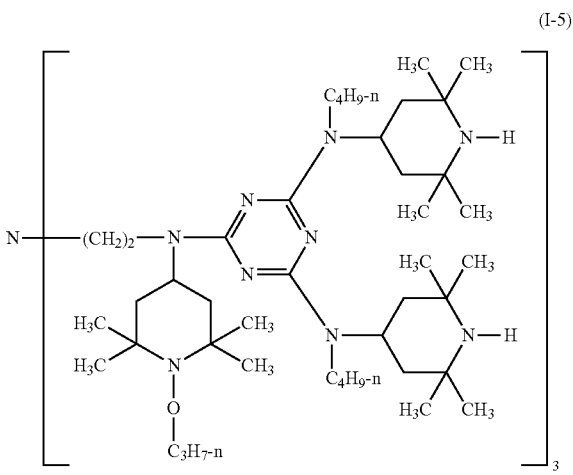

(I-5)

5A) Preparation of the Intermediate of the Formula

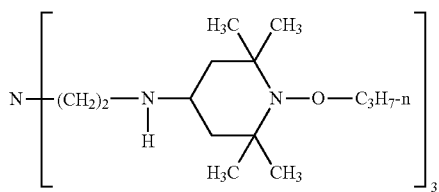

A four-necked round-bottom flask equipped with a mechanical stirrer, thermocouple, dropping funnel and condenser is charged with 30.0 g of 1-n-propoxy-2,2,6,6-tetramethyl-piperidin-4-one, 7.7 g of tris(2-aminoethyl)amine and 350 ml of cyclohexane. The solution is heated at reflux for 3 hours and the water is removed. Then, it is cooled at room temperature and 120 ml of MeOH are added at 15° C. Subsequently, 4.0 g of NaBH$_4$ is slowly added at 15° C. The solution is finally wormed up and stirred at room temperature overnight. It is washed twice with 200 ml of H$_2$O and 200 ml of CH$_2$Cl$_2$. The solvent is removed under reduced pressure to give a yellow-orange solid which is purified by precipitation from cold acetone. The desired product is obtained as a white powder, filtered and dried under vacuum at 80° C.

Yield: 24.5 g (63% of theory)

TGA (Air, 10° C./min): 210° C.: −0.15%; 260° C.: −3.83%

ESI-MS in THF/CH$_3$CN: [M]$^+$: 738.9

Melting point: 126-129° C.

5B) Preparation of the Intermediate of the Formula

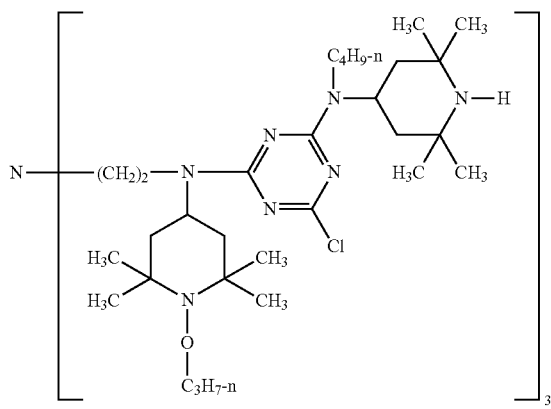

A four-necked round-bottom flask equipped with a mechanical stirrer, thermocouple, dropping funnel and condenser is charged with 9.85 g of the intermediate described under 5A, 14.42 g of 2-[N-(2,2,6,6-tetramethylpiperidin-4-yl)-n-butylamino]-4,6-dichloro-1,3,5-triazine and 9.1 ml of NaOH (30%) dissolved in 60 ml of toluene. The reaction is heated at 85° C. overnight. The solution is then cooled down and washed several times with water until pH=7. The solvent is removed and the obtained product is dissolved in 8 ml of CH$_2$Cl$_2$. The product is obtained as yellow-white powder upon precipitation from cold MeOH.

Yield: 21.8 g (95.8% of theory)

TGA (Air, 10° C./min): 130° C.: −0.03%; 250° C.: −0.11%

Elemental Analysis: C: 62.94% (99.6%); H: 9.67% (99.4%); N: 17.95% (99.6%); O: 2.77% (98.6%)

ESI-MS: Direct infusion: [M+H]$^+$: 1711

5C) Preparation of the Compound of the Formula (I-5)

A four-necked round-bottom flask equipped with a mechanical stirrer, thermocouple, dropping funnel and condenser is charged with 21.4 g of the intermediate described under 5B, 7.97 g of N-(2,2,6,6-tetramethylpiperidin-4-yl)-n-butylamine and 7.81 ml of NaOH (30%) dissolved in 100 ml of xylene. The reaction is heated at reflux overnight and the water is removed. The solution is then cooled down and washed several times with water until pH=7. The solvent is removed and the obtained product is dissolved in 20 ml of CH$_2$Cl$_2$. The desired product is obtained as a white-yellow powder upon precipitation from cold CH$_3$CN.

Yield: 23.8 g (90.9% of theory)

TGA (Air, 10° C./min): 260° C.: −0.18%; 300° C.: −2.46%

Elemental Analysis: C: 68.64% (99.1%); H: 10.83% (97.7%); N: 17.39% (99.2%); O: 2.13% (99.1%).

Maldi-Tof (Matrix Assisted Laser Desorption/Ionisation-Time of flight mass spectrometer; alfa-Cyano-4-hydroxycinnamic acid): [M+H]$^+$: 2238

Melting point: 118-123° C.

EXAMPLE 6

Preparation Of The Compound Of The Formula (I-6)

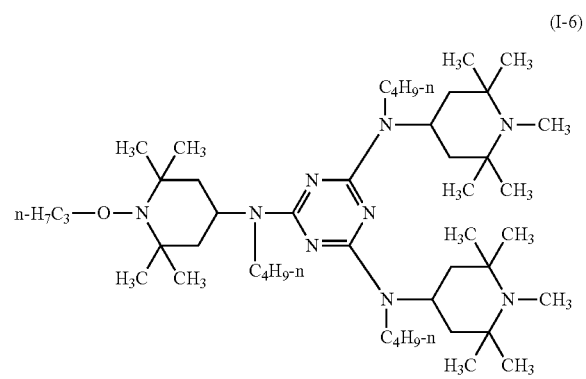

A 200 ml steel autoclave equipped with a mechanical stirrer is loaded with 9.1 g of 2,4-bis[N-(1,2,2,6,6-pentamethylpiperidin-4-yl)-n-butylamino]-6-chloro-1,3,5-triazine, 6.17 g of 1-n-propoxy-2,2,6,6-tetramethyl-4-(butylamino) piperidine, 3.2 g of aqueous NaOH (30%) and 50 ml of xylene. The mixture is heated at 160° C. for 18 hours. After cooling to ambient temperature, the aqueous phase is removed and the organic phase is repeatedly washed with water. The organic phase is dried over sodium sulfate and concentrated in vacuo. The crude product is heated at 60° C. and 0.025 mbar for 12 hours to give a yellowish product.

Yield: 11.4 g (88% of theory)

TGA (Air, 10° C./min): 210° C.: −0.35%; 260° C.: −5.83%

ESI-MS: Direct infusion: [M+H]$^+$: 798

$^1$H-NMR (400 MHz): 5.24 (2H), 3.72 (2H), 3.30 (6H), 2.29 (6H), 1.73-1.45 (18H), 1.38-1.05 (44H), 1.00-0.85 (12H)

EXAMPLE 7

Preparation Of The Compound Of The Formula (I-7)

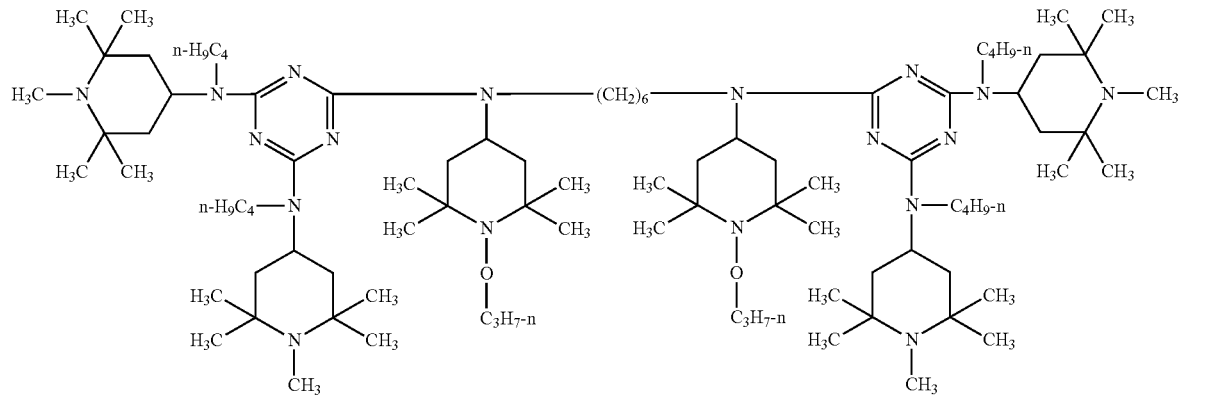

(I-7)

A 200 ml steel autoclave equipped with a mechanical stirrer is loaded with 23.4 g of 2,4-bis[N-(1,2,2,6,6-pentamethylpiperidin-4-yl)-n-butylamino]-6-chloro-1,3,5-triazine, 10.0 g of N,N'-bis[1-propoxy-2,2,6,6-tetramethypiperidin-4-yl]hexane-1,6-diamine, 7.8 g of aqueous NaOH (30%) and 80 ml of xylene. The mixture is heated at 160° C. for 18 hours. After cooling to ambient temperature, the aqueous phase is removed and the organic phase is repeatedly washed with water. The organic phase is dried over sodium sulfate and concentrated in vacuo. The crude product is heated at 60° C. and 0.025 mbar for 12 h to give a yellowish product (Yield: 16.0 g (52.3% of theory). A portion of this product is dissolved in a minimum amount of xylene and dropped into methanol. The desired product is isolated as a pure, white powder.

TGA (Air, 10° C./min): 210° C.: −0.21%; 260° C.: −2.83%

ESI-MS: Direct infusion: $[M+H]^+$: 1565

$^1$H-NMR (400 MHz): 5.23 (4H), 3.73 (4H), 3.34 (12H), 2.27 (12H), 1.78-1.45 (41H), 1.45-1.06 (85H), 1.05-0.84 (18H)

EXAMPLE A

Film manufacture: In a turbo mixer (Caccia (RTM), Labo 10) the additives listed in Table 1 are mixed with LDPE (Low Density Polyethylene) at an overall 10% by weight concentration keeping the 4:1 ratio reported in Table 1. The mixture is extruded at a maximum temperature of 200° C. to granules using an O.M.C. twin-screw extruder (model ebv 19/25). The granules are subsequently mixed and diluted with the same LDPE in order to obtain the final composition for preparing a 150 μm thick film, using a blow-extruder (Dolci (RTM)) working at a maximum temperature of 210° C. The final concentrations of the LDPE films are indicated in Table 1.

TABLE 1

| Final composition of the LDPE films | |
|---|---|
| Film No. | Additives |
| Film 1 | 0.4% Compound 1 |
|  | 0.1% of Antioxidans A |
| Film 2 | 0.4% of Compound 2 |
|  | 0.1% of Antioxidans A |

TABLE 1-continued

| Final composition of the LDPE films | |
|---|---|
| Film No. | Additives |
| Film 3 | 0.4% of Compound 3 |
|  | 0.1% of Antioxidans A |

"%" means % by weight, relative to the LDPE.

Antioxidans A:
(Irganox 1010 (RTM)) Tetrakis[3-(3,5-di-tert-butyl-4-hydroxyphenyl)-propionyloxymethyl]methane Test Methods:
Light Exposure: The LDPE films obtained are exposed in an ATLAS Weatherometer (model Ci65A) equipped with a 6500W Xenon lamp (0.35 W/m$^2$; continuous light cycle, black panel temperature=63° C.).

Vapam Treatment: The LDPE films obtained are placed in a close chamber and exposed to the vapors of a 0.74 v/v solution of VAPAM® (Sodium N-methyldithiocarbamate 39.1 WT %) in water. The final volume is 2000 ml. The system is kept at 30° C. for 20 days. Then, the LDPE films are subjected to light exposure as described above.

Evaluation Parameters:
1) Carbonyl increment (CO): Evaluation of the carbonyl band increment (1710 cm-1) in function of the exposure time is monitored with a FT-IR Perkin-Elmer (RTM) Spectrum One.
2) Tensile elongation @ break: Evaluation of elongation % property is carried out with a ZWICK Z1.0 (RTM) testing machine: speed: 100 mm/min; holder distance: 30 mm; Temperature: 20° C.

The results are listed in Tables 2 to 4.

TABLE 2

Carbonyl increment of a 150 μm LDPE film after hours (h) of light exposure

| | Carbonyl increment *) | | | | | |
|---|---|---|---|---|---|---|
| | 0 h | 474 h | 1479 h | 2490 h | 3988 h | 4992 h |
| Film 1 | 0.000 | 0.000 | 0.003 | 0.003 | 0.009 | 0.013 |
| Film 2 | 0.000 | 0.001 | 0.004 | 0.006 | 0.009 | 0.013 |
| Film 3 | 0.000 | 0.000 | 0.001 | 0.003 | 0.006 | 0.011 |

*) Low values are desired.

TABLE 3

Carbonyl increment of a 150 μm LDPE film after hours (h) of light exposure and VAPAM treatment

| | Carbonyl increment *) | | | | |
|---|---|---|---|---|---|
| | 0 h | 554 h | 1451 h | 2059 h | 2532 h |
| Film 1 | 0.000 | 0.000 | 0.007 | 0.013 | 0.023 |
| Film 2 | 0.000 | 0.007 | 0.011 | 0.024 | 0.035 |
| Film 3 | 0.000 | 0.02 | 0.008 | 0.016 | 0.028 |

*) Low values are desired.

TABLE 4

Tensile elongation @ break of a 150 μm LDPE film after hours (h) of light exposure and VAPAM treatment

| | Tensile elongation @ break **) | | |
|---|---|---|---|
| | 0 h | 2556 h | 3490 h |
| Film 1 | 100 | 100 | 94 |
| Film 2 | 100 | 93 | 88 |
| Film 3 | 100 | 99 | 96 |

**) High values are desired.

The invention claimed is:

1. A compound of the formula (I):

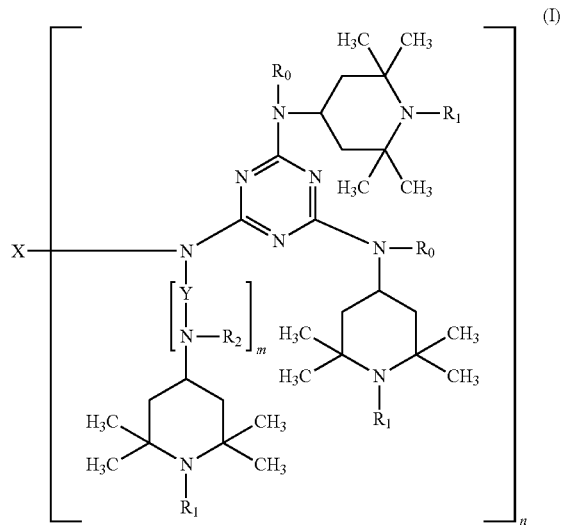

wherein:

one or two radicals of the radicals $R_1$ are independently of one another $C_1$-$C_{20}$alkyloxy or $C_3$-$C_{12}$cycloalkyloxy and the remaining radicals $R_1$ are independently of one another hydrogen, $C_1$-$C_{20}$alkyl or $C_3$-$C_{12}$cycloalkyl;

the radicals $R_0$ and $R_2$ are independently of one another hydrogen, $C_1$-$C_{20}$alkyl, $C_3$-$C_{12}$cycloalkyl or a group of the formula (II-a)

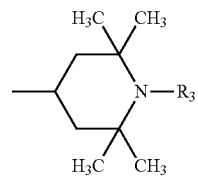

with $R_3$ being hydrogen, $C_1$-$C_{20}$alkyl, $C_3$-$C_{12}$ cycloalkyl, $C_1$-$C_{20}$alkyloxy or $C_3$-$C_{12}$cycloalkyloxy;

Y is $C_2$-$C_{12}$alkylene;

m is 1;

n is 2 or 3;

when n is 2, X is $C_2$-$C_{12}$alkylene; and when n is 3, X is a group N(Z—)$_3$ with Z being $C_2$-$C_{12}$alkylene.

2. A compound according to claim 1 wherein:

one or two radicals of the radicals $R_1$ are independently of one another $C_1$-$C_{10}$alkyloxy or $C_3$-$C_6$cycloalkyloxy and the remaining radicals $R_1$ are independently of one another hydrogen, $C_1$-$C_{10}$alkyl or $C_3$-$C_6$cycloalkyl;

the radicals $R_0$ and $R_2$ are independently of one another hydrogen, $C_1$-$C_{10}$alkyl, $C_3$-$C_6$cycloalkyl or a group of the formula (II-a);

the radicals $R_3$ are independently of one another hydrogen, $C_1$-$C_{10}$alkyl, $C_3$-$C_6$cycloalkyl, $C_1$-$C_{10}$alkyloxy or $C_3$-$C_6$cycloalkyloxy;

Y is $C_2$-$C_8$alkylene;

m is 1;

n is 2 or 3;

when n is 2, X is $C_2$-$C_8$alkylene; and when n is 3, X is a group N(Z—)$_3$ with Z being $C_2$-$C_8$alkylene.

3. A compound according to claim 1 wherein one or two radicals of the radicals $R_1$ are independently of one another $C_1$-$C_4$alkyloxy or cyclohexyloxy and the remaining radicals $R_1$ are independently of one another hydrogen, $C_1$-$C_4$alkyl or cyclohexyl;

the radicals $R_0$ and $R_2$ are independently of one another hydrogen, $C_1$-$C_4$alkyl, cyclohexyl or a group of the formula (II-a);

the radicals $R_3$ are independently of one another hydrogen, $C_1$-$C_4$alkyl, cyclohexyl, $C_1$-$C_4$alkyloxy or cyclohexyloxy;

Y is $C_2$-$C_6$alkylene;

m is 1;

n is 2 or 3;

when n is 2, X is $C_2$-$C_6$alkylene; and when n is 3, X is a group N(Z—)$_3$ with Z being $C_2$-$C_6$alkylene.

4. A compound according to claim 1, wherein:

one or two radicals of the radicals $R_1$ are propoxy and the remaining radicals $R_1$ are independently of one another hydrogen or methyl.

5. A composition, comprising:
A) an organic material subject to degradation induced by light, heat or oxidation; and
B) a compound of claim 1.

6. A composition according to claim 5, further comprising at least one of the following components:
(C-I) a filler or reinforcing agent,
(C-II) a pigment,
(C-III) a further light stabilizer, (C-IV) a processing additive,
(C-V) an antioxidant,
(C-VI) a terpene derivative.

7. A composition according to claim 5, wherein the organic material A) is a thermoplastic natural or synthetic polymer.

8. A composition according to claim 5 wherein the organic material A) is a polyolefin homo- or copolymer, a starch modified polyolefin or a starch based polymer composite.

9. A composition according to claim 5, wherein the organic material a) is a polyethylene, a polypropylene, a polyethylene copolymer or a polypropylene copolymer.

10. A shaped article made of a composition according to claim 5.

11. A shaped article according to claim 10, which is a film, fibre, profile, pipe, bottle, tank or container.

12. A shaped article according to claim 10, which is a mulch film.

13. A method for stabilizing an organic material against degradation induced by light, heat or oxidation, which comprises incorporating into the organic material at least one compound of claim 1.

* * * * *